(12) United States Patent
Offringa et al.

(10) Patent No.: US 10,373,519 B1
(45) Date of Patent: Aug. 6, 2019

(54) SYSTEM AND METHOD FOR DETERMINING AND PROVIDING ACTIVITY RECOMMENDATIONS

(71) Applicant: Glooko Inc., Mountain View, CA (US)

(72) Inventors: Reid Offringa, San Francisco, CA (US); Michael S. Greenfield, Mountain View, CA (US)

(73) Assignee: Glooko Inc., Mountain View, CA (US)

( * ) Notice: Subject to any disclaimer, the term of this patent is extended or adjusted under 35 U.S.C. 154(b) by 450 days.

(21) Appl. No.: 15/340,578

(22) Filed: Nov. 1, 2016

Related U.S. Application Data

(63) Continuation-in-part of application No. 15/276,070, filed on Sep. 26, 2016.

(51) Int. Cl.
*A61B 5/00* (2006.01)
*A61B 5/145* (2006.01)
*G09B 19/00* (2006.01)

(52) U.S. Cl.
CPC ........ *G09B 19/003* (2013.01); *A61B 5/14532* (2013.01); *A61B 5/7242* (2013.01); *A61B 5/7264* (2013.01)

(58) Field of Classification Search
CPC . G09B 19/003; A61B 5/7242; A61B 5/14532; A61B 5/7264
See application file for complete search history.

(56) References Cited

U.S. PATENT DOCUMENTS

| | | | |
|---|---|---|---|
| 5,319,355 A | 6/1994 | Russek | |
| 8,653,965 B1 | 2/2014 | Otto et al. | |
| 9,292,475 B1 | 3/2016 | Crane et al. | |
| 9,446,194 B2 * | 9/2016 | Kamath | A61B 5/14532 |
| 2006/0251114 A1 | 11/2006 | Nuggehalli et al. | |
| 2007/0231209 A1 | 10/2007 | Cosentino et al. | |
| 2007/0299318 A1 | 12/2007 | Chen et al. | |
| 2008/0097908 A1 | 4/2008 | Dicks et al. | |
| 2008/0281840 A1 | 11/2008 | Fennell et al. | |
| 2009/0054743 A1 | 2/2009 | Stewart | |
| 2009/0112626 A1 | 4/2009 | Talbot et al. | |
| 2009/0296742 A1 | 12/2009 | Sicurello et al. | |

(Continued)

OTHER PUBLICATIONS

Dalal et al., "Method and System for Monitoring a Medical Condition," U.S. Appl. No. 14/014,179, filed Aug. 29, 2013.

*Primary Examiner* — Jacqueline Cheng
*Assistant Examiner* — Tho Q Tran
(74) *Attorney, Agent, or Firm* — Hawley Troxell Ennis & Hawley LLP; Sean P. Lewis

(57) ABSTRACT

A method and apparatus for determining and providing activity recommendations includes receiving glucose level data and activity data. The glucose level data is formed into two or more data sets, with each set representing a different time period. Each data set is evaluated and ranked against each other set according to one or more of several different individual factors and the individual ranking for each set are combined, resulting in an overall ranking for given data sets. A highest ranked data set is then determined, which is associated thereby with a highest ranked time period. Activities of the activity data which took place within the highest ranked time period are provided as recommendations to the user to encourage greater numbers of times those activities are undertaken.

39 Claims, 10 Drawing Sheets

(56) References Cited

U.S. PATENT DOCUMENTS

| | | |
|---|---|---|
| 2010/0075353 A1* | 3/2010 | Heaton ................ A61B 5/0002 435/14 |
| 2010/0094098 A1 | 4/2010 | Smith et al. |
| 2013/0045685 A1 | 2/2013 | Kiani |
| 2013/0212168 A1 | 8/2013 | Bonasera et al. |
| 2014/0132413 A1 | 5/2014 | Fox et al. |
| 2014/0222446 A1 | 8/2014 | Ash et al. |

* cited by examiner

After weighting, best day is now Tuesday, not Monday

Alpha = 2

| Day | SD | AUC | Tmean | Tmax/min |
|---|---|---|---|---|
| Mon | 30 | 1500 | 1.2 | 1.20 |
| Tue | 14 | 1600 | 1.6 | 1.10 |

Rank order →

| Day | SD | AUC | Tmean | Tmax/min |
|---|---|---|---|---|
| Mon | $2^2 = 4$ | 1 | 1 | $2^2 = 4$ |
| Tue | $1^2 = 1$ | 3 | 2 | $1^2 = 1$ |

Mean rank

BEST DAY

| Day | rank |
|---|---|
| Mon | 2.50 |
| (Tues) | 1.75 |

FIG. 10

SYSTEM AND METHOD FOR DETERMINING AND PROVIDING ACTIVITY RECOMMENDATIONS

RELATED APPLICATION

This application is a continuation-in-part of Offringa, et al., U.S. patent application Ser. No. 15/276,070 (GLOO-003), filed on Sep. 26, 2016, entitled "SYSTEM AND METHOD FOR DETERMINING AND PROVIDING ACTIVITY RECOMMENDATIONS," which is herein incorporated by reference in its entirety as if it were fully set forth herein.

BACKGROUND

Modern medical science includes many devices for gathering data regarding the health status of an individual, and for providing that data to a healthcare provider so that the healthcare provider may use that data to diagnose a medical condition of an individual, adjust the patient's treatment plan or for other reasons.

The individual's glucose level, as a first example, may be determined through various means, such as through the use of a glucose monitor or meter, a single glucose measurement using a sample, or through the use of a glucose monitor, such as a glucose monitor that uses a sensor placed under the skin to analyze interstitial fluid (a.k.a., Continuous Glucose Monitor or CGM), or non-invasively analyzes the body to determine the glucose level (e.g., through an optical sensor that analyzes an ear lobe), or otherwise, after which the determined glucose level is provided to and/or otherwise used by a healthcare provider to assess a current condition of the individual. Glucose level is one of many characteristics that may provide insight into the health of the individual.

In another example, a pressure measuring device may be used to determine a pressure of a patient, after which the pressure measurement is provided to and/or otherwise used by a healthcare provider to assess a current condition of the patient.

Both pressure level and glucose level are examples of characteristics that often vary widely for a given individual over a period of time depending on various factors such as activities the individual might currently be doing, might have recently been doing, whether those activities are consistently undertaken, whether the activities are performed just once, etc. It is often quite difficult to determine whether a given instance of an activity contributed positively or negatively to a given pressure level or glucose level or series of pressure or glucose levels.

SUMMARY

According to one or more embodiments, glucose level data of an individual is collected over any desired time span, for example, over a 7-day, a 14-day or a 30-day time span, as well as any desired frequency, for example once ever 5 minutes, once every hour, once every day, 3 times per week, etc. For the purposes of this discussion, the resulting set of glucose level data shall be referred to as a glucose data set. The collected glucose level data may be continuous, but is not necessarily continuously collected, and may or may not include data from each hour of a given day, or even from each day.

According to one or more embodiments, glucose level data of the glucose data set is separated into different glucose subsamples, according to desired time periods associated with the glucose data and each glucose subsample. The glucose subsamples are then analyzed through the determination of and ranking of several factors determined from individual ones of the glucose subsamples.

Once each glucose subsample is ranked against each other glucose subsample, the highest-ranked glucose subsample is selected, and activities are determined that the individual has participated in during the same time period that is associated with the highest ranked glucose subsample. Recommendations are then formed from those activities associated with the highest ranked glucose subsample and presented to the individual and/or a healthcare provider associated with the individual.

More particularly, according to one or more embodiments, a system and method for determining and providing activity recommendations includes receiving, as a glucose data set, glucose level data representing multiple glucose level readings of an individual taken over time. The glucose level readings may be taken manually or automatically, through sampling of blood, interstitial fluid, or any other body fluid, directly, indirectly, through continuous or intermittent sampling, or through other means.

According to one or more embodiments, the system and method further include forming, from the glucose data set, two or more glucose subsamples, each having glucose level data, where each glucose subsample of glucose level data represents individual glucose level readings taken within a given time period of interest. According to various embodiments, a time period is a 24-hour period of time, or 48 hours, or 4, 6, 8, or 12 hours, or any other length of time, depending on the granularity of the raw data and the result desired. Time periods may include blocks of time in the morning, during lunchtime, afternoon, evening or late evening, or nighttime, or any other suitable time period desired by an implementer of the processes described herein.

According to one or more embodiments, the system and method further include receiving activity data representing one or more activities performed by the individual, with at least one activity being associated with respect to each of the various time periods associated with the glucose subsamples, or at least within a predetermined amount of time of the various time periods. The activity data may be received from a variety of activity data sources, including from the individual, with the activity data being received through a computing system user interface, or from one or more electronic devices associated with an activity, such as an apparatus that captures a number of steps taken in a day, etc., or through other means.

According to one or more embodiments, the system and method further include determining one or more factors associated with the glucose subsamples. According to one or more embodiments, the factors include one or more of an average area under the curve, a standard deviation, results of a biotransform algorithm performed on each individual glucose reading of the glucose subsample, and a min-max total. Details regarding the determination of these factors are provided below.

According to one or more embodiments, the system and method further include ranking each glucose subsample against each other glucose subsample, the rankings being at least partly based on one or more of the factors, In one embodiment, each glucose subsample is individually ranked against each other glucose subsample according to a first one of the factors, followed by each glucose subsample being individually ranked against each other glucose subsample according to a second one of the factors, and so on, for each factor being considered, resulting in each glucose subsample having individual ranks for each factor. According to one or more embodiments, individual rankings associated with a given glucose subsample are combined, resulting on an overall ranking for the glucose subsample, after which a highest ranked glucose subsample is selected, based on the overall rankings.

According to one or more embodiments, the system and method further include determining a highest ranked time period associated with the highest ranked glucose subsample.

Associated with the highest ranked time period when the glucose data of the highest ranked glucose subsample was taken are activities that the individual performed which have likely positively influenced the individual's glucose levels. Therefore, using the time period of the highest ranked glucose subsample, a determination of those activities may be made, and further instances of those activities may be recommended. The processes described herein are intended to benefit the technical fields of medicine, user experience, data processing and high speed data analysis. Further, there is no abstraction to the concepts and algorithms described herein, due to their highly detailed and complex nature.

BRIEF DESCRIPTION OF THE DRAWINGS

FIGS. 9 and 10 show charts reflecting how a third weighting factor is applied, according to one embodiment.

Figure 1:
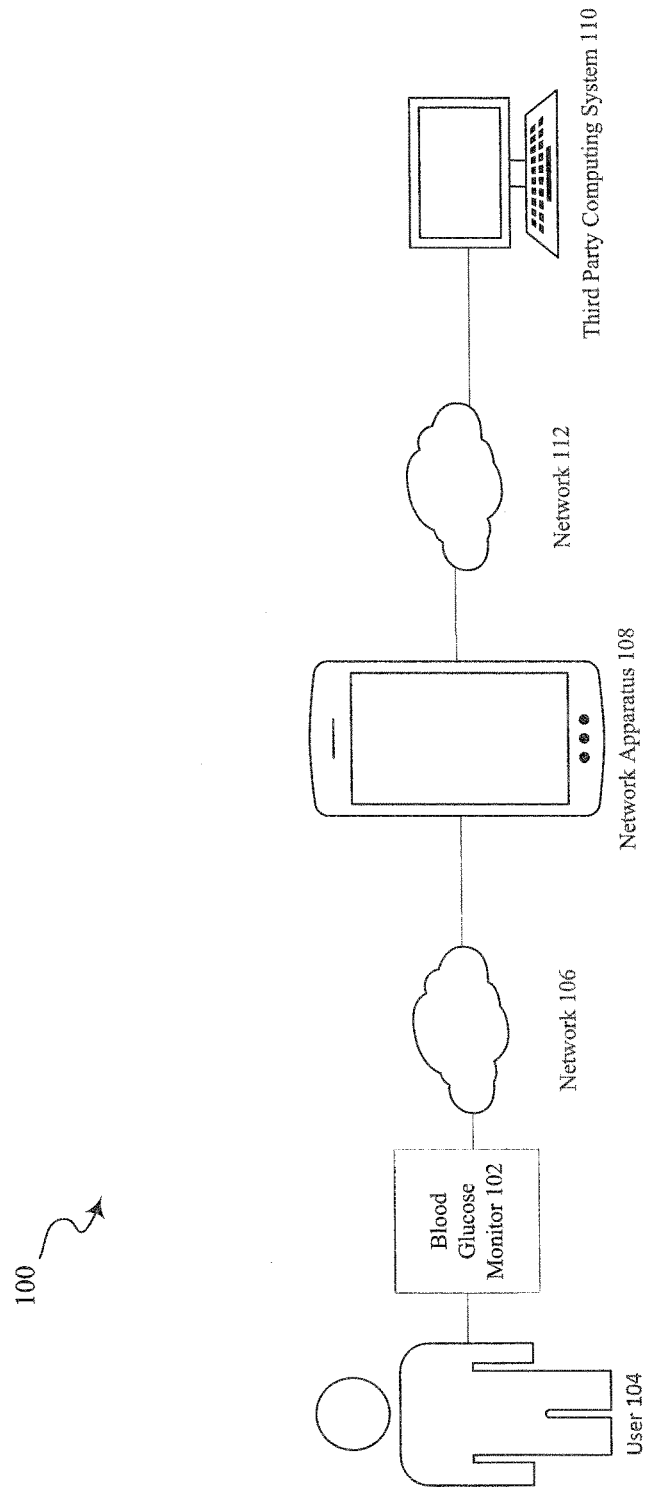
FIG. 1 is a system diagram of an exemplary architecture for one embodiment of a system for determining and providing activity recommendations.

Common reference numerals are used throughout the drawing figures and the detailed description to indicate like elements. One skilled in the art will readily recognize that the above drawing figures are examples and that other architectures, modes of operation, orders of operation and elements/functions can be provided and implemented without departing from the features of the invention, as set forth in the claims.

DETAILED DESCRIPTION

Glucose levels may change for a wide variety of reasons including patient activity. It is often not easy to recall what activities a given person participated in on a given day in the past, much less what activities they might have participated in for each given day over the past several weeks. Further, what works well for one individual might not work as well for another, since the activities one person undertakes in a given day might be much different from the activities a different person undertakes on the same day. By employing the techniques and processes described herein, particular activities associated with good glucose level readings for particular individuals may be determined, and personalized recommendations provided that are specific to the given individual.

Embodiments will now be discussed with reference to the accompanying drawings, which depict one or more exemplary embodiments. Embodiments may be implemented in many different forms and should not be construed as limited to the specific embodiments set forth herein, shown in the drawings, and/or described below. Rather, these exemplary embodiments are provided to allow a disclosure of the principles of the invention, as set forth in the claims, to those of skill in the art.

In one embodiment, a process for determining and providing activity recommendations includes one or more applications, such as software packages, modules, or systems, formed as a series of process operations and implemented on and executed by one or more computing systems. Process operations discussed herein may be evidenced as a single software application executing on a single computing system, or may instead be evidenced as a collection of modules performed or executed over several different computing systems. In one embodiment, subsets of the process operations are stored in and are executed by one or more computing systems, with others of the process operations being stored in a local or remote data storage location, such as a database coupled to computing systems through a network, and loaded into the one or more computing systems for execution as needed.

As used herein, the term "computing system" includes, but is not limited to, virtual or hardware-based platforms, local or remote computing systems, a desktop computing system; a portable computing system; a mobile computing system; a laptop computing system; a notebook computing system; a tablet computing system; a workstation; a server computing system; a mobile phone; a smart phone; a wireless telephone; a two-way pager; a Personal Digital Assistant (PDA); a media player, i.e., an MP3 player and/or other music and/or video player; an Internet appliance; or any device that includes components that can execute all, or part, of any one of the processes and/or operations as described herein.

In addition, as used herein, the term computing system, can denote, but is not limited to, systems made up of multiple desktop computing systems; portable computing systems; mobile computing systems; laptop computing systems; notebook computing systems; tablet computing systems; workstations; server computing systems; smart phones; wireless telephones; two-way pagers; Personal Digital Assistants (PDAs); media players; Internet appliances; or any devices that can be used to perform the processes and/or operations as described herein.

As used herein, the term "network" includes, but is not limited to, any wired or wireless network or network system such as, but not limited to, a peer-to-peer network, a hybrid peer-to-peer network, a Local Area Network (LAN), a Wide Area Network (WAN), a public network, such as the Internet, a private network, a bluetooth network, a cellular network, a POTS network; any general network, communications network, or general network/communications network system; a wireless network; a wireless and wired combination network; a satellite network; a cable network; any combination of different network types; or any other system capable of allowing communication between two or more computing systems, whether available or known at the time of filing or as later developed.

FIG. 1 is a system diagram of an exemplary architecture for one embodiment of a system for determining and providing activity recommendations.

Referring to FIG. 1, system 100 includes a glucose monitor 102 configured to determine a current glucose level of a user, for example, user 104. Glucose monitors, such as glucose monitor 102, are, in one embodiment, enabled to determine a current glucose level when manually or remotely triggered, at regular predetermined intervals, or at custom intervals set by the user or by a designer of the glucose monitor.

Within a short time before, during, or after a glucose level is determined, a time associated with the glucose level is determined as well. The time associated with a glucose level may be determined in any combination of several ways. For example, the glucose monitor may have a time clock built into it and may record the time and the glucose level in a memory of the glucose monitor prior to the time data and the glucose data being transferred for other processing. Alternatively, following the glucose level being determined, glucose data representing that glucose level may be transferred to a remote data storage, such as a database or other data storage located within network apparatus 108 which is coupled to glucose monitor through network 106. When the remote data store receives the glucose data, that glucose data is stored, in various embodiments, along with a time the glucose data was received from the glucose monitor.

According to one or more embodiments, glucose level data of an individual is collected from one or more sources, manually or automatically, over any desired time span, for example, over a 7-day, a 14-day or a 30-day time span, as well as any desired frequency, for example once ever 5 minutes, once every hour, once every day, 3 times per week, etc. For the purposes of this discussion, the resulting set of glucose level data shall be referred to as a glucose data set. The collected glucose level data is not necessarily continuously collected, and may or may not include data from each hour of a given day, or even from each day.

As mentioned above, system 100 further includes network apparatus 108 which is operatively coupled to glucose measurement device 102 through network 106.

Herein, a "network apparatus" includes, but is not limited to: any computing system, a smart phone, a cellular phone, a digital wireless telephone, a tablet computing system, a notebook computing system, any portable computing system, a two-way pager, a Personal Digital Assistant (PDA), a media player, i.e., an MP3 player and/or other music and/or video player, a server computer, an Internet appliance, or any other device and/or computing system that includes components that can execute all, or part, of any one of the processes and/or operations as described herein.

In addition, as used herein, the term network apparatus, can denote, but is not limited to, computing systems made up of multiple wired and wireless devices, cellular telephones, digital telephones, two-way pagers, PDAs, media players, or any desired combination of these devices and/or computing systems, that are coupled to perform the processes and/or operations as described herein.

According to various embodiments, smartphones and other mobile computing systems are connected, and/or otherwise operably coupled, to one or more mobile communication networks and/or other networks, such as, but not limited to, any general network, communications network, or general network/communications network system, a cellular network, a wireless network, a combination of different network types, or other wireless, wired, and/or a wireless and wired combination network, a public network, a private network, a satellite network, a cable network, or any other network capable of allowing communication between two or more computing systems, as discussed herein, and/or available or known at the time of filing, and/or as developed after the time of filing.

Network apparatus 108 is further coupled to third party computing system 110 through network 112. Network 112 can be any network or network system as defined herein, and/or known in the art at the time of filing, and/or developed after the time of filing, enabled to facilitate and/or allow communication between two or more network enabled devices, such as network apparatus 108 and third party computing system 110.

Third party computing system 110 typically includes components (not shown) known to those of ordinary skill in the art, including, but not limited to a central processing unit (CPU), an input/output (I/O) interface, and a memory system, including cache memory. In one embodiment, a memory system of third party computing system 110 includes all, or part, of a process for determining and providing activity recommendations, described below, and that process is evidenced by machine-readable instructions executed by a CPU of a computing system as described herein.

As an additional example, in one embodiment, a memory system of third party computing system 110 includes a portion of a process for determining and providing activity recommendations and downloads other portions as needed. Additional portions of a process for determining and providing activity recommendations may be provided for execution by one or more computing systems by one or more other network accessible locations, such as a third party server, a third party database, or any other network accessible storage known in the art at the time of filing or developed after the time of filing.

In yet another example, a memory system of third party computing system 110 includes a portion of a process for determining and providing activity recommendations and that portion interacts with other portions that are performed or executed by other computing systems. Instructions to perform one or more of the process operations described herein may also be embedded and executed by a specially designed custom hardware component such as an Application Specific Integrated Circuit (ASIC), a programmable logic array, or any other component suitable for performing the one or more process operations. Such a custom hardware component may be designed into any one or more of the components and computing systems discussed herein, such as third party computing system 110.

As discussed herein, during the same time periods when glucose level data is collected and stored, activity data is also collected and optionally remotely stored. In various embodiments, third party computing system 110 includes a computerized activity data collector, such as a device that determines how many steps a person takes over a given time period. Such a device records, in one embodiment, activity data each time period, such as each minute, each hour, each day, or any other relevant time period, and either stores the activity data locally or transfers that activity data to a remote data storage area, such as a storage area present within network apparatus 108. Any of the features of network apparatus 108 may also or alternatively be present within third party computing system 110.

Glucose level data and activity data is collected over any desirable time span as well as frequency and then analyzed as discussed herein. Although there is no upper or lower bound on the number of activities or glucose level readings that are received for each time period, more data occasionally provides higher quality results. Therefore, a number of glucose level readings of at least 100 is desirable in some situations. Additionally, over 300 glucose level readings is acceptable, but will not necessarily produce higher quality results.

Following receipt of, and optional remote storage of glucose data representing a glucose data set, the glucose data set is used to form two or more different glucose subsamples, according to times associated with each glucose level of the glucose data set and desired time periods associated with each glucose subsample.

Process operations are performed on the data in order to determine one or more factors of each glucose subsample and then rank the different glucose subsamples against each other to determine a highest ranked glucose subsample. Determining factors and characteristics associated with each glucose subsample may be accomplished through specialized software or hardware modules of one or more computing systems and/or of glucose monitor 102. For example, specialized software or hardware modules of either network apparatus 108 or third party computing system 110 may accomplish executing process operations to determine factors and characteristics associated with each glucose subsample. The process operations may be performed as one or more glucose level readings of the glucose level data are received, at regular intervals, or according to criteria specified by a user or other individual.

The process operations discussed herein may be performed very quickly, in order to provide a user timely feedback which may be incorporated into their lifestyle and make changes while the circumstances surrounding the best glucose levels and associated activities are fresh in a user's mind. An additional advantage of the process described herein is that a user may receive valuable information about improving lifestyle without needing to constantly interact with physicians and other high-cost medical experts.

Figure 2:
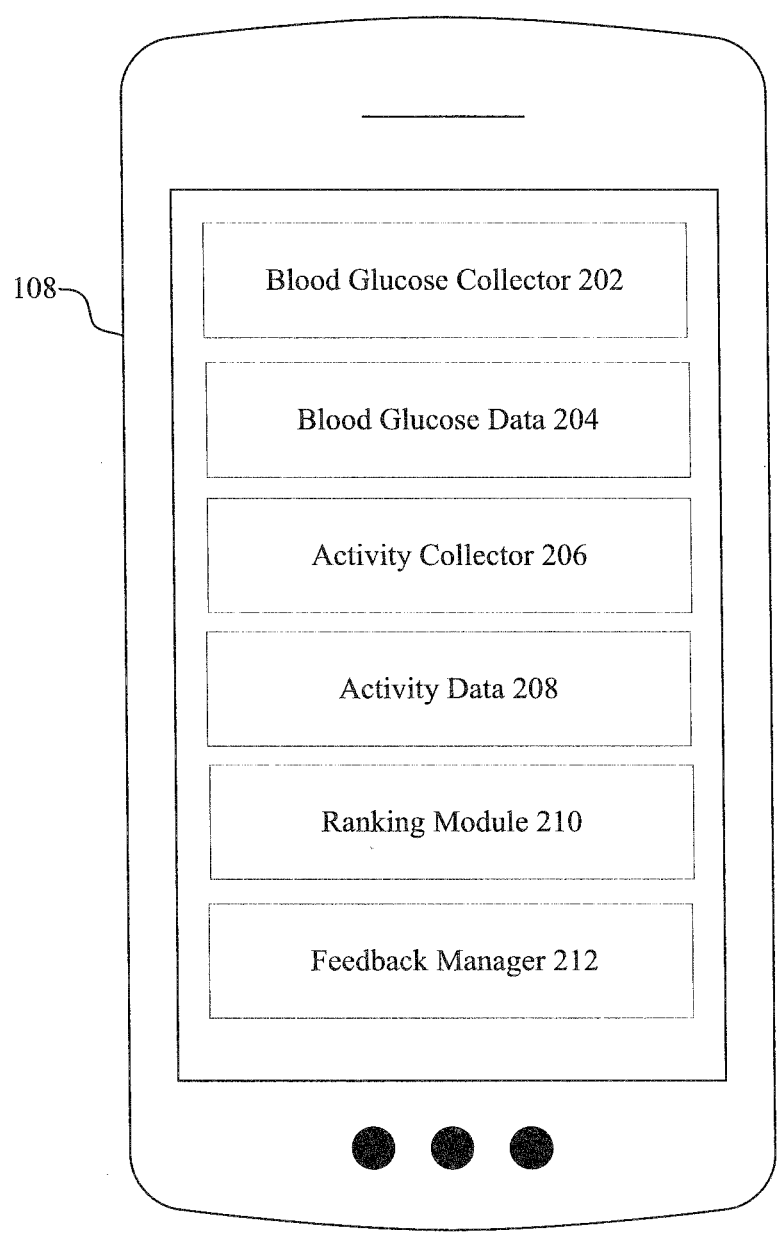
FIG. 2 is a block diagram depicting a network apparatus in accordance with various embodiments.

FIG. 2 is a block diagram depicting a network apparatus in accordance with various embodiments.

Referring to FIG. 2, network apparatus 108 includes one or more of glucose collector 202, glucose data 204, activity collector 206, activity data 208, ranking module 210, and feedback manager 212.

In various embodiments, glucose collector 202 is configured to receive glucose level data from glucose monitor 102. As discussed herein, glucose monitor 102 may be configured to determine glucose levels and times those glucose levels were determined, and store glucose level data corresponding to those times within glucose monitor 102. In this configuration, glucose monitor 102 may store the glucose data until glucose collector 202 requests it, after which glucose monitor 102 sends the glucose data to glucose collector 202. Glucose collector 202 then receives the glucose data from glucose monitor 102 and stores the received glucose data and associated times in a database provided for that purpose, such as glucose data 204. Herein when reference is made to determining times associated with glucose levels, it is meant that one or more of a time of day, calendar date, day of week, day of month, Julian date or some other form of date and/or time are determined.

In various embodiments, glucose collector 202 is configured to receive glucose level data from glucose monitor 102 as individual components of glucose data, each component representing a single glucose level which is not accompanied by a time of day, calendar date or other indication of time, as discussed herein. In this configuration, glucose collector 202 receives glucose data from glucose monitor 102 and stores the received glucose data in a database provided for that purpose, such as glucose data 204. In this configuration, there may be a need to determine a time corresponding to a glucose level, if that time isn't provided by glucose monitor 102. In this case, a time may be added to glucose data 204 by glucose collector 202 which corresponds to a time when the glucose data was received by glucose collector 202. When reference is made that time is "added" to glucose data 204, it is meant that the time and the glucose data it is associated with are both linked in some way.

In various embodiments, activity collector 206 is configured to receive activity data from a wide variety of activity data sources. For example, if any of glucose monitor 102, network apparatus 108, or third party computing system 110 is configured to collect exercise data such as a number of steps an individual takes, activity collector 206 is, in that embodiment, configured to receive the activity data and record a time span when the activity took place, based on the received activity data including time references. In this configuration, activity collector 206 receives activity data from an activity data source and stores the received activity data in a database provided for that purpose, such as activity data 208. On occasion, there may be a need to determine a time corresponding to an activity that was undertaken, if that time isn't provided by the activity data source. In this case, a time may be added to activity data 208 by activity collector 206. In various embodiments, the time added to activity data 208 with respect to a given set of activity data corresponds to a time when the activity data was received by activity collector 206.

It is contemplated that activity data sources include any user or other individual, or any device providing input into network apparatus 108, glucose monitor 102, or third party computing system 110. In one embodiment, a user or other individual enters activity data through a user interface of glucose monitor 102, network apparatus 108 or third party computing system 110. In one embodiment, activity data is captured through an activity-based device, such as an activity device that captures a number of steps an individual walks or a device such as a treadmill that captures data regarding a distance the individual walks or runs, or any other activity-based device. Such an activity device is intermittently, periodically, or continuously coupled to system 100 so that activity data may be captured and utilized as discussed herein. The examples of activity devices discussed herein are not intended to be limiting, and it is intended that many other such devices be enabled for the capture and transfer of activity data to the process operations discussed herein.

As to ranking module 210, according to various embodiments, the stored glucose data 204 is analyzed by ranking module 210 to determine a highest ranked time period associated with most desirable glucose levels of the glucose data.

According to one or more embodiments, the glucose data stored at glucose data 204 is separated by ranking module 210 into different glucose subsamples, according to the time associated with the particular glucose data. In one instance, it may be desirable to use a 24-hour time period, such as days of the week, days of the month, or a similar time period. If, for example, the desired time periods are days of the week, glucose data of glucose data 204 is formed into glucose subsamples where each glucose subsample represents a different 24-hour period, where the 24 hours corresponds to different days of the week. Thus, for example, if it is desired to form glucose subsamples according to portion of a day, glucose subsamples may be formed according to periods corresponding to morning, perhaps 6 to 11 am, lunch, perhaps 11 through 2 pm, afternoon, perhaps 2 pm through 6 pm, dinner time, perhaps 6 pm through 9 pm, and the like, or any other time periods desired by a designer or of a user of the system and method described herein. Definitions of particular time periods may be provided by a system developer, or alternatively by a user or other individual through a user interface of network apparatus 108, provided remotely from a user interface or stored data of a third party computing system, such as third party computing system 110, or through any other mechanism known to those of ordinary skill or later developed.

Once formed, the different glucose subsamples are then analyzed, using ranking module 210, according to one or more factors associated with individual ones of the glucose subsamples. According to one or more embodiments, the factors include one or more of an average area under the curve, a standard deviation, results of performing a biotransform algorithm on the subsample, and a min-max total. Additional detail as to how these factors are determined is provided below. Other factors are contemplated, and may be desirable to use, either together with one or more of the factors described herein, or by themselves, without departing from the subject matter of this disclosure.

Once each glucose subsample is ranked against each other glucose subsample, a highest-ranked glucose subsample is selected, and the timeframe associated with the highest ranked subsample set is used to query activity data 208 to determine one or more activities that the individual has participated in during the time period associated with that highest ranked glucose subsample.

Once one or more activities that the individual has participated in during the time period associated with the highest ranked glucose subsample have been determined, feedback manager 212 of network apparatus 108 may be used, in one embodiment, to prepare and present a user interface for the user reflecting an indication of which time period has been determined to be associated with the highest ranked, and therefore most desirable, glucose subsample, together with an optional additional presentation of the one or more determined activities. For example, if it is determined that the individual participated in 30 minutes of biking, or, for example, 15 minutes of aerobic activity, or walked one thousand steps during the determined time period, an indication of which time period was the highest ranked is provided to the individual together with an optional presentation that the 30 minutes of biking, or the 15 minutes of aerobic activity, or walking the one thousand steps likely contributed to the desired goal, which is to have better glucose readings. Thus, the individual is presented with concrete results showing real world activities that they can participate in more frequently which will achieve a desired goal of controlling their glucose levels doing activities they like.

Additional detail on the process operations of the system and method will now be provided.

Figure 3:
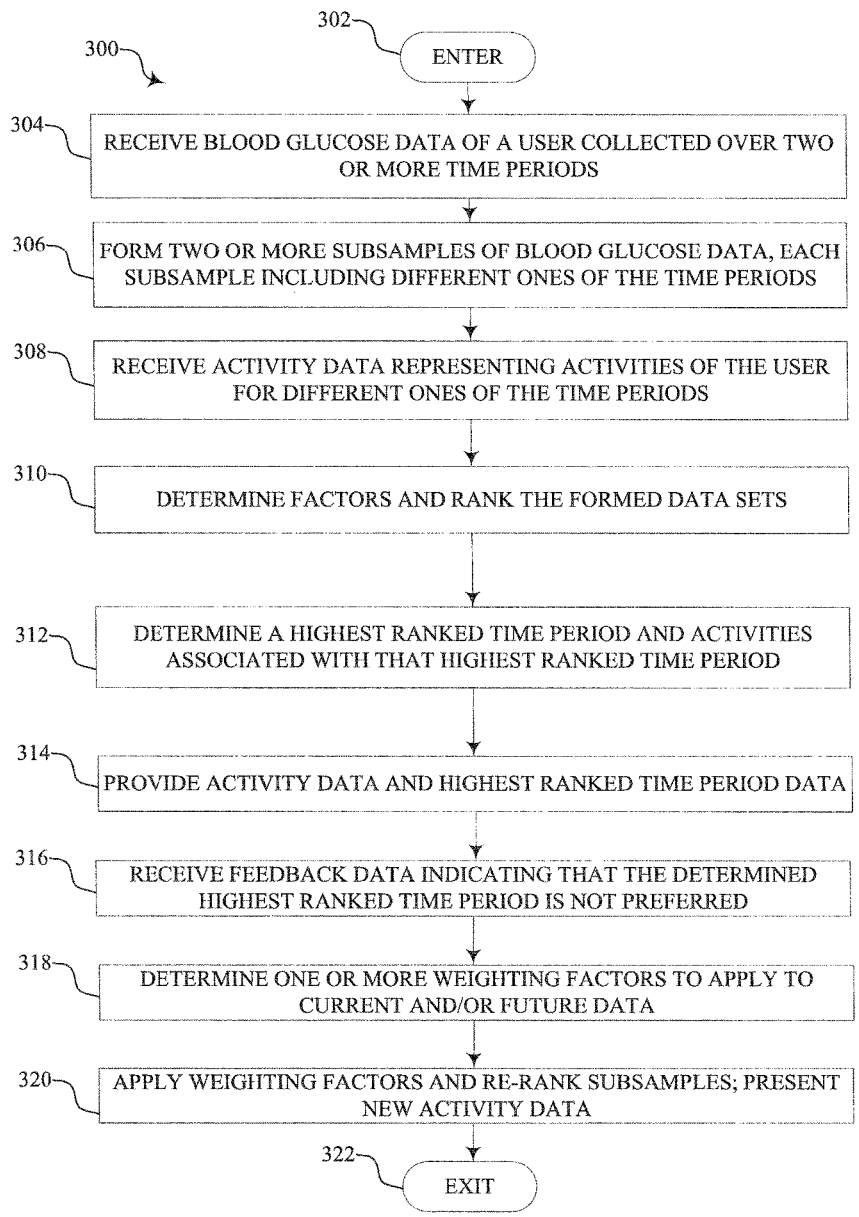
FIG. 3 is a process diagram showing a process for determining and providing activity recommendations in accordance with one embodiment.

FIG. 3 is a process diagram showing a process for determining and providing activity recommendations in accordance with one embodiment.

In one embodiment, as discussed herein, at least a portion of process 300 executes on a single computing system, such as network apparatus 108 or third party computing system 110.

Referring to FIG. 3, process 300 begins at block 302 and proceeds to block 304. At block 304, glucose data of an individual is received by process 300 indirectly or directly from a glucose monitoring device, such as glucose monitor 102. Such glucose monitors, such as glucose monitor 102, are often enabled to determine a current glucose level when manually or remotely triggered, at regular predetermined intervals, or at custom intervals set by the user or set by a designer of the glucose monitor.

At some point before, during, or after a glucose level is determined, for example by glucose monitor 102, a time associated with the glucose level is determined as well. The time associated with a glucose level may be determined several ways. For example, the glucose monitor may have a time clock built into it and may record the time and the glucose level in a memory of the glucose monitor prior to the time data and the glucose data being further processed. Alternatively, following the glucose level being determined, glucose data representing that glucose level may be transferred to a remote data storage, such as data storage located within network apparatus 108 which is coupled to glucose monitor through network 106. When the remote data store receives the glucose data, that glucose data is, in various embodiments, stored along with a time the glucose data was received from the glucose monitor.

According to one or more embodiments, glucose level data of an individual is collected over any desired time span, for example, over a 7-day, a 14-day or a 30-day time span as well as any desired frequency, for example once every 5 minutes, once every hour, once every day, 3 times per week, etc. For the purposes of this discussion, the resulting set of glucose level data shall be referred to as a glucose data set. The collected glucose level data is not necessarily continuously collected, and may or may not include data from each hour of a given day, or even from each day.

After enough glucose level data has been received, such as following the collection of glucose level data over a desired span of time, process flow continues at block 306 where two or more subsamples of glucose data are formed from the glucose data set, such as from glucose data 204.

According to one or more embodiments, at least some of the glucose data stored at glucose data 204 is separated into different glucose subsamples, according to times associated with the individual glucose level readings of the glucose data.

In one example, it may be desirable to form the glucose subsamples based a 24-hour time period, such as according to days of the week, days of the month, or a similar time period. In this example, the glucose subsamples would be formed according to which day the particular glucose level data was collected. For example, if the desired time periods are days of the week, glucose data of glucose data 204 would be formed into glucose subsamples representing different 24-hour periods representing different days of the week. If, in another example, it is desired to form glucose subsamples according to portion of a day, glucose subsamples may be formed according to periods corresponding to morning, perhaps 6 to 11 am, lunch, perhaps 11 through 2 pm, afternoon, perhaps 2 pm through 6 pm, dinner time, perhaps 6 pm through 9 pm, and the like, or any other time periods desired by a designer or of a user of the process operations discussed herein. More complex processing may also be used, forming glucose subsamples of all Monday mornings for the past month, for example, or such as forming glucose subsamples of Monday mornings and Wednesday evenings, or in other ways, without departing from the teachings provided herein.

Definitions of particular time periods may be provided by a system developer, or alternatively by a user or other individual through a user interface of network apparatus 108, provided remotely from a user interface or stored data of a third party computing system, such as third party computing system 110, or through any other mechanism known to those of ordinary skill or later developed.

At block 308, within a predetermined amount of time before, during or after glucose data is received at block 304, activity data representing activities of the user, i.e. the same individual associated with the glucose level readings, are received.

Various ways of collecting the activity data are contemplated. In various embodiments, third party computing system 110 is a computerized activity data collector, such as a device that determines how many steps a person takes over a given time period, or a treadmill, or other cardio-based device. Such a device records activity data, and optionally records time data regarding a time when the activities occur and transfers that activity data and time data to a remote data storage area, such as a storage area present on network apparatus 108.

Activity collector 206, in various embodiments, is configured to receive activity data from a wide variety of activity data sources. For example, if glucose monitor 102 is configured to collect activity data such as a number of steps an individual takes, activity collector 206 is, in that embodiment, configured to receive the activity data from glucose monitor 102 and attribute the activity data to the correct time period, based on the received activity data including time references as to when the activity took place. In this configuration, activity collector 206 receives activity data from glucose monitor 102 and stores the received activity data in a database provided for that purpose, such as activity data 208.

On occasion, there may be a need to determine a time corresponding to an activity that was undertaken, if that time isn't provided by the source of the activity data, such as by glucose monitor 102 or third party computing system 110. In this case, a time may be added to activity data 208 by activity collector 206. In various embodiments, the time stored within activity data 208 with respect to a given set of activity data received from an activity data source corresponds to a time when the activity data was received by activity collector 206.

It is contemplated that activity data sources include any user, other individual, or any device providing input into network apparatus 108, glucose monitor 102, or third party computing system 110. In one embodiment, a user or other individual enters activity data through a user interface of one or more of glucose monitor 102, network apparatus 108 and third party computing system 110. In one embodiment, activity data is captured through an activity-based device, such as an activity device that captures a number of steps an individual walks or a treadmill that captures data regarding a distance the individual walks or runs. Such an activity device is intermittently, periodically, or continuously coupled to system 100 so that activity data may be captured and utilized as discussed herein. The examples of activity devices discussed herein are not intended to be limiting, and it is intended that many other such activity devices be enabled for the capture and transfer of activity data to the process operations discussed herein.

Once activity data representing activities of the user for at least two different time periods has been received, process flow continues, in various embodiments, at block 310 where factors are determined with respect to the glucose sub samples formed at block 306.

Ranking module 210, according to various embodiments, uses the stored glucose data 204 to determine a highest ranked time period associated with glucose data of a highest ranked glucose subsample.

To determine a highest ranked time period, the different glucose subsamples are analyzed, using ranking module 210, according to several factors. According to one or more embodiments, the factors include one or more of an average area under the curve, a standard deviation, results of performing a biotransform algorithm on each individual glucose level of the glucose subsample, and a min-max total.

Figure 4:
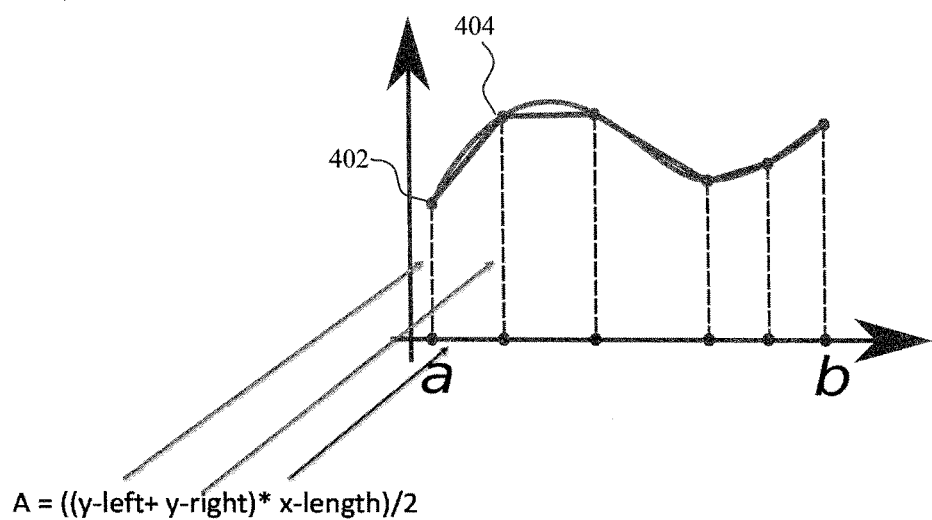
FIG. 4 is a pictorial view of how area under the curve is determined according to one embodiment.

FIG. 4 is a diagram showing a determination of area under the curve in accordance with one embodiment.

In one embodiment, successively taken glucose readings from a given formed glucose subsample are used to determine an average area under the curve. Prior to determining an area under the curve, an adjustment is made for glucose values of the glucose subsample that are outside a predetermined range where glucose values are considered to be normal or otherwise acceptable. In one embodiment, the predetermined range for acceptable values is bounded by an upper threshold glucose level and a lower threshold glucose level. The upper threshold glucose level may range, in one embodiment, between 150 and 250 and may, for example, be a value of 180. The lower threshold glucose level may range, in one embodiment, between 50 and 80 and may, for example, be a value of 70.

In various embodiments, prior to determining an average area under the curve, for each original glucose level of the glucose subsample that is at or above the upper threshold glucose level, a value of the upper threshold glucose level is subtracted from the original glucose level and the result is used in further area under the curve process operations in place of the original glucose level.

In various embodiments, prior to determining an average area under the curve, for each original glucose level of the glucose subsample that is at or below the lower threshold glucose level, a value of the lower threshold glucose level is subtracted from the original glucose level, and the result is squared. The squared result is used in further area under the curve process operations in place of the original glucose level.

FIG. 4 is a pictorial view of how area under the curve is determined according to one embodiment. Referring to FIG. 4, first glucose level reading 402 is summed with second glucose level reading 404 and the result is multiplied by a numerical value representative of a length of elapsed time between when each of the two readings were taken. That result is then divided by two. This process for determining area under the curve is repeated for each successive pair of glucose level readings in the glucose subsample, e.g. glucose level readings 2 and 3, 3 and 4, 4 and 5, etc. until all successive glucose level readings of the glucose subsample have been used. All areas under the curve for that glucose subsample are then averaged, resulting in a final average area under the curve for all data points in the glucose subsample which will be used later when the glucose subsamples are ranked against each other. Other methods of determining an area under the curve for three, four or more successive glucose readings will be evident to a person of ordinary skill familiar with this disclosure.

A second factor which may be used in ranking the formed glucose data sets is standard deviation. Like average area under the curve, a standard deviation is determined for each formed glucose data set and then compared, during the ranking process, against the standard deviations of each other formed glucose data set.

Standard deviation of a formed glucose data set may be determined using the formula below.

$$s_N = \sqrt{\frac{1}{N}\sum_{i=1}^{N}(x_i - \bar{x})^2},$$

In order to determine the standard deviation of a glucose subsample, the mean of the glucose subsample is first found by adding each glucose level reading of the glucose subsample and dividing by the number of glucose level readings of the glucose subsample, resulting in a mean of the glucose subsample.

Next, a difference is obtained of each glucose level reading of the glucose subsample from the mean of the glucose subsample determined above. Then, square each obtained difference. Finally, average these squared differences and take the square root, resulting in a standard deviation of the glucose subsample. A standard deviation found for each glucose subsample will be used later when the factors associated with the glucose subsamples are ranked.

A third factor which may be used in ranking the glucose subsamples is an average of the results of a biotransform algorithm performed on each out of range glucose level of a glucose subsample. Similar to the process operations for average area under the curve discussed above, a biotransform algorithm result is determined for each out of range glucose level of the glucose subsample and then the entire set of biotransform algorithm results is averaged and compared, during the ranking process, against the average result of the biotransform algorithm of each other glucose subsample.

In various embodiments, prior to performing the biotransform algorithm on a given glucose level of a glucose subsample, an assignment is made, for each original glucose level of the glucose subsample that is at or below a high end acceptable glucose level and also at or above a low end acceptable glucose level, that the result of the performed biotransform algorithm for that original glucose level is a value of zero, and no other biotransform algorithm steps are performed for that glucose value of the formed glucose data set. The high end acceptable glucose level with respect to this factor may range, in one embodiment, between 110 and 130 and may be a value of 120. The low end acceptable glucose level with respect to this factor may range, in one embodiment, between 60 and 80 and may be a value of 70.

In various embodiments, the upper threshold glucose level and the lower threshold glucose level discussed above may or may not be the same respective values as the high end acceptable glucose level and low end acceptable glucose level discussed herein with respect to other factors.

For each original glucose level of the glucose subsample that is above the predetermined high end acceptable glucose level the following biotransform is applied to the glucose level:

biotransform result=(1.2*((log(Glucose level)1.09)−constant))2 where the constant can be any number between 4 and 8. In one embodiment, the constant is approximately 5.28.

For each original glucose level of the glucose subsample that is below the predetermined low end acceptable glucose level the following biotransform algorithm is applied to the glucose level:

biotransform result=(2.28*((log(Glucose level)1.09)−constant))2 where the constant can be any number between 4 and 8. In some embodiments, the constant is approximately 5.28.

As discussed above, similar to the process operations for average area under the curve discussed above, a biotransform algorithm result is determined for each out of range glucose level of the glucose subsample and then the entire set of biotransform algorithm results is averaged and compared, during the ranking process, against the average result of the biotransform algorithm of each other glucose subsample.

A fourth factor which may be used in ranking the glucose subsample is a min-max of the results of the biotransform algorithm discussed above, performed on each out of range glucose level of a glucose subsample. If the biotransform algorithm is implemented and performed in a given system and method performing process operations described herein, the results of performing that biotransform algorithm may be used in the performance of this fourth factor.

To determine the fourth factor, with respect to a given glucose subsample, an examination of the biotransform results of the third factor takes place, to identify a highest biotransform value and a lowest biotransform value, with respect to the glucose subsample.

Following the identification of a highest biotransform value and a lowest biotransform value for the glucose subsample, the highest biotransform value and the lowest biotransform value are summed, and the result is used in the ranking processes described below.

Following the determination of the one or more factors to be used to rank the various glucose subsamples, each glucose subsample is ranked against each other glucose subsample at block 310. The ranking process includes, in various embodiments, considering each factor for each glucose subsample independently of the other factors. Thus, a first factor is considered for all glucose subsamples, followed by a second factor being considered for all glucose subsamples, etc. In one embodiment, lower results for each factor are more desirable than higher numbers for those factors. Thus, in one embodiment, individual factor results for a first glucose subsample when compared with a second glucose subsample would result in the first glucose subsample being ranked higher than the second glucose subsample, with respect to that particular factor.

All average area under the curve results for all formed glucose data sets are examined and assigned a rank according to how a given average area under the curve result compares to other average area under the curve results. Correspondingly, all standard deviation results for all formed glucose data sets are examined and assigned a rank according to how a given standard deviation results compares to other standard deviation results. Similarly, ranking takes place with respect to other factors and glucose subsamples as well.

Figure 5:
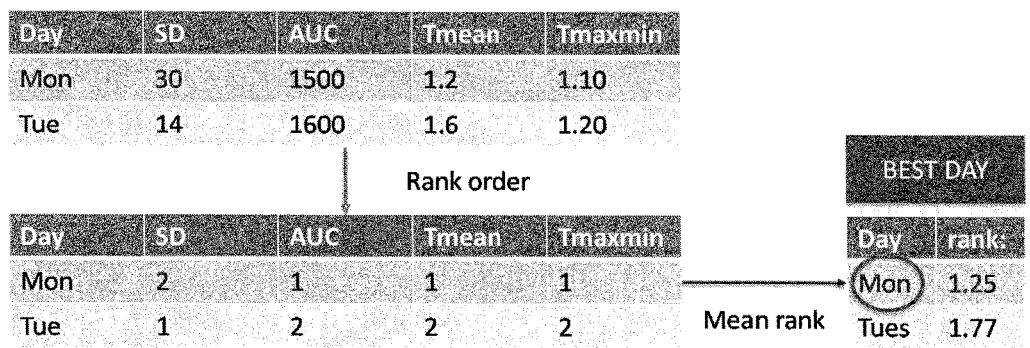
FIG. 5 shows a chart reflecting ranking of formed glucose subsamples according to one embodiment.

FIG. 5 shows a chart reflecting ranking of glucose subsamples according to one embodiment. In the example of FIG. 5, two glucose subsamples have been formed around days of the week, with each glucose subsample including 24 hours of glucose data. Results of standard deviation, area under the curve, the biotransform algorithm and the min-max of the results of the biotransform algorithm are shown for both of the glucose subsamples.

As can be seen from the chart of FIG. 5, the standard deviation for Monday's glucose subsample is 30 and the standard deviation for Tuesday's glucose subsample is 14.

Using a rule where a lower standard of deviation is desired, Monday is ranked lower, e.g. less desirable, than Tuesday, for that factor. Further, using a paradigm ranking the various factors using 1 as the best, with higher numbers representing less desirable glucose subsamples as to that factor, Monday's standard deviation is given a rank of 2, whereas Tuesday's standard deviation is given a rank of 1.

The area under the curve for Monday's glucose subsample is 1500 and the area under the curve for Tuesday's glucose data set is 1600. Using a rule where a lower area under the curve is more desirable than a higher area under the curve, Monday is ranked higher than Tuesday, for that factor. Further, using a paradigm ranking the various factors using 1 as the best, with higher numbers representing less optimum glucose subsamples as to that factor, Monday's area under the curve is given a rank of 1, whereas Tuesday's area under the curve is given a rank of 2.

The result of the biotransform algorithm process operations for Monday's glucose subsample is 1.2 and the results of the biotransform algorithm process operation for Tuesday's glucose subsample is 1.6. Using a rule where a lower biotransform algorithm process operation result is more desirable than a biotransform algorithm process operation result. Monday is ranked higher than Tuesday, for that factor. Further, using a paradigm ranking the various factors using 1 as the best, with higher numbers representing less best glucose subsamples as to that factor, Monday's biotransform algorithm process operation result is given a rank of 1, whereas Tuesday's biotransform algorithm process operation result is given a rank of 2.

Finally, the max-min result for Monday's glucose data set is 1.1 and the max-min result for Tuesday's glucose subsample is 1.2. Using a rule where a lower max-min result is more desirable than a higher max-min result, Monday is ranked higher than Tuesday, for that factor. Further, using a paradigm ranking the various factors using 1 as the best, with higher numbers representing less optimum glucose subsamples as to that factor, Monday's max-min result is given a rank of 1, whereas Tuesday's max-min result is given a rank of 2.

Following ranking individual factors of individual glucose subsamples, the ranking results for each glucose subsample are averaged, resulting in the glucose subsample for Monday receiving an overall rank of 1.25 and the glucose subsample for Tuesday receiving an overall rank of 1.77. Since, in this example, a ranking is more desirable if it has a lower number, Monday's glucose subsample is considered better than Tuesday's glucose subsample.

At block 312, a highest ranked time period is the time period associated with the highest ranked glucose subsample. Therefore, the highest ranked time period in the example is the 24-hour time period including Monday.

Proceeding with block 314, activity data and highest ranked time period data is developed from the result formed at block 312. In the example, Monday was determined to be the highest ranked time period. Thus, activity data associated with Monday is copied or otherwise used to produce, at block 314, one or more user interfaces reflecting that Monday was a "best day" and emphasizing activities performed on Monday, with the intent that the user perform one or more of the Monday activities more frequently.

Figure 6:
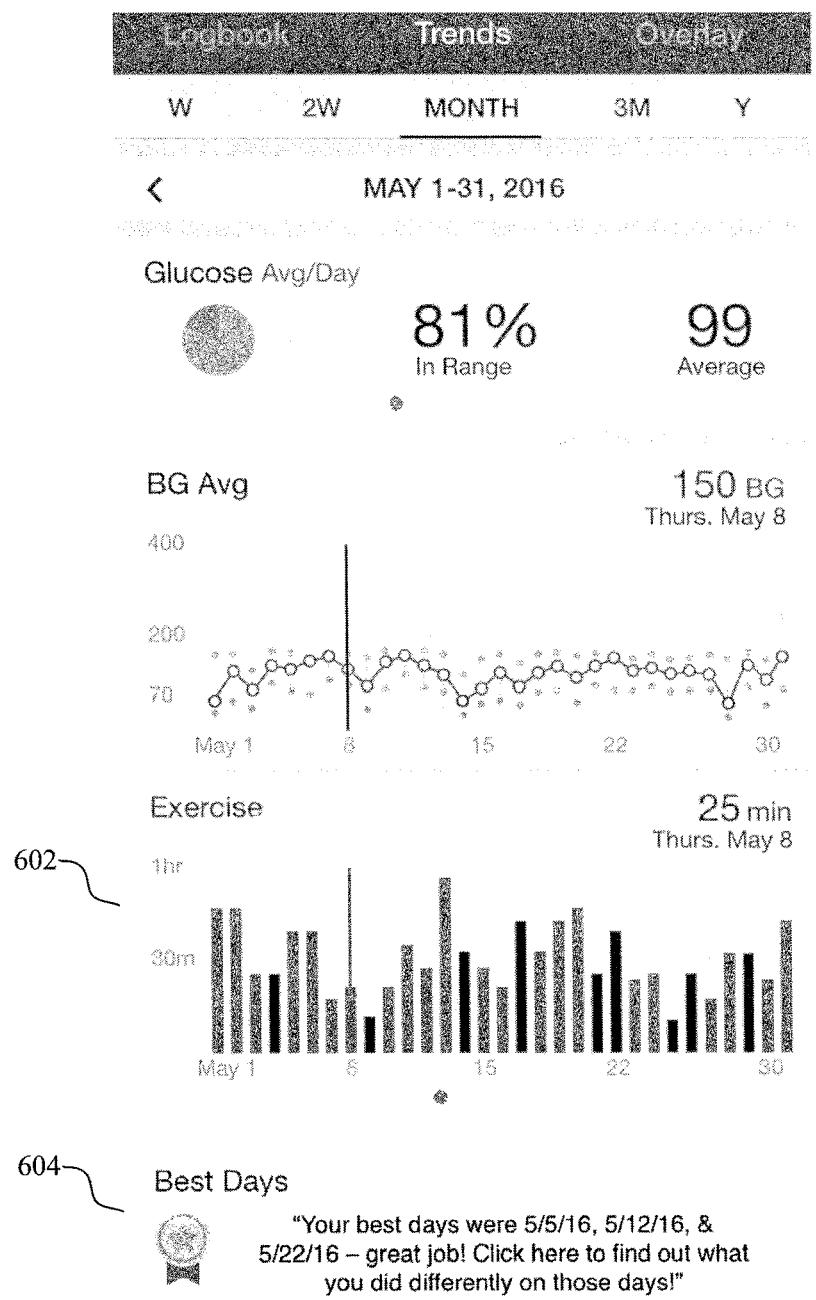
FIG. 6 depicts a user interface according to various embodiments.

FIG. 6 depicts a user interface according to various embodiments. Referring to FIG. 6, activity data for the month of May is displayed at 602 showing how long the individual exercised on a given day. Further, three "best days," e.g. days ranked highly according to the glucose data and the factors discussed herein, are depicted at 604 in an area which when activated by the individual causes the process to display additional activity specific to the best days.

In the previous discussion, day of week was used as a primary example of how to form glucose subsamples. However, it isn't always the case that day of week is the best option, since, although people generally are creatures of habit, people's activities often vary widely over a given week or month.

In one embodiment, glucose subsamples are formed based on four to six-hour segments of time, such as morning, afternoon, evening, and night. The factors discussed herein are then determined for each of the glucose subsample. Using a Guassian Mixture Model and Latent Class Analysis, glucose subsamples are clustered in order to determine best glucose subsamples regardless of day or date.

In one embodiment, best clusters are compared to less-best clusters to determine characteristics of the best clusters that could be repeated to increase the likelihood of getting a higher number of best clusters. Best clusters may also be compared to worst clusters to better understand characteristics of the less than best or worst clusters. Less than best and worst clusters may be associated with activities that should be done a fewer number of times. Commonalities for best clusters may include, but are not limited to, particular activities, e.g. exercise, what they ate, whether they took their prescribed medications and a degree of compliance with the timing and quantity of medication taken, and places visited.

Again, once one or more activities that the individual has participated in during the time period associated with the highest ranked glucose data set have been determined, feedback manager 212 of network apparatus 108 may be used, in one embodiment, to prepare and present a user interface, at block 314, for the user reflecting at least an indication of which time period has been determined to be highest ranked, together with an optional additional presentation of the one or more determined activities. For example, if it is determined that the individual participated in 30 minutes of biking, or, for example, 15 minutes of aerobic activity, or walked one thousand steps during the highest ranked time period, an indication of which time period was the highest ranked time period is provided to the individual together with an optional presentation that the 30 minutes of biking, or the 15 minutes of aerobic activity, or walking the one thousand steps likely contributed to the desired goal, which is to have better glucose readings over future time periods. By presenting the activity and glucose data in this manner, the individual is presented with concrete results showing real world activities that they can participate in more frequently which will achieve a desired goal.

In one embodiment, feedback data is received at block 316, through feedback manager 212 or another suitable module, the feedback data indicating that the determined highest ranked time period isn't the preferred highest ranked time period, for one or more reasons. In one embodiment, the feedback data is received from a primary source such as through a user interface prepared by feedback manager 212 and operated by a user associated with the glucose level data and the activity data. In one embodiment, at least a portion of the feedback data is received from a secondary source such as a physician or other practitioner.

In one embodiment, the feedback data received at block 316 includes one or more an indication of one or more reasons the previously determined highest ranked time period is not preferred. In one embodiment, the one or more reasons include an average glucose of the previously determined highest ranked time period being too high. In one embodiment, the one or more reasons include an average glucose of the previously determined highest ranked time period being too low. In one embodiment, the one or more reasons include the variability or variance of the glucose levels of the previously determined highest ranked time period being too high.

In one embodiment, once feedback data has been received at block 316, one or more weighting factors are determined at block 318 which are applied at block 320 to current data, such as the glucose subsamples previously formed at block 306, or future data, such as one or more glucose subsamples of a different consideration set or glucose subsamples including glucose data collected at a different time, or factors associated with the glucose subsamples, or any combination thereof. In one embodiment, one or more weighting factors are applied to one or more of the previously determined factors. In one embodiment, the particular weighting factor and/or the particular way the weighting factor is applied or otherwise used is based on contents of the received feedback data, such as the one or more reasons the previously determined highest ranked time period is not preferred.

In one embodiment, a first weighting factor is determined and applied to area under the curve data associated with each glucose subsample of the current consideration set. In one embodiment, the first weighting factor is applied to a high portion, e.g. those glucose levels of the glucose subsamples of the current consideration set that are above an upper threshold, of the area under the curve data associated with each glucose subsample of the current consideration set. In one embodiment, the upper threshold is 120.

In one embodiment, the first weighting factor is applied to a low portion, e.g. those glucose levels of the glucose subsamples of the current consideration set that are below a lower threshold, of the area under the curve data associated with each glucose subsample of the current consideration set. In one embodiment, the lower threshold is 70.

Any desired weighting factor may be used. In one embodiment, the first weighting factor is of the form $$w_{pm} = 1 + \left| \frac{x_i - x_{i+1}}{7 * SD_{pm}} \right|$$

where $x_i$ and $x_{i+1}$ respectively refer to glucose data values of the previously determined glucose subsample. In one embodiment, to determine which glucose data values of a given glucose subsample are used to determine a weighting factor, the glucose data values of the given glucose subsample are first sorted from high to low. In one embodiment, the first weighting factor is determined using the highest and second-highest glucose level values of the given glucose data sample, for $x_i$ and $x_{i+1}$ respectively. In one embodiment, the first weighting factor is applied at block 320 to one or more of the factors previously determined at block 310. In one embodiment, more than one weighting factor is determined, and each is applied to different portions of data included in the glucose subsamples or different factors associated with the glucose subsamples. Weighting factors may be applied through multiplication, addition, subtraction, division, raising or lowering a value by a power of the weighting factor, or through any other desirable application.

Figure 7:
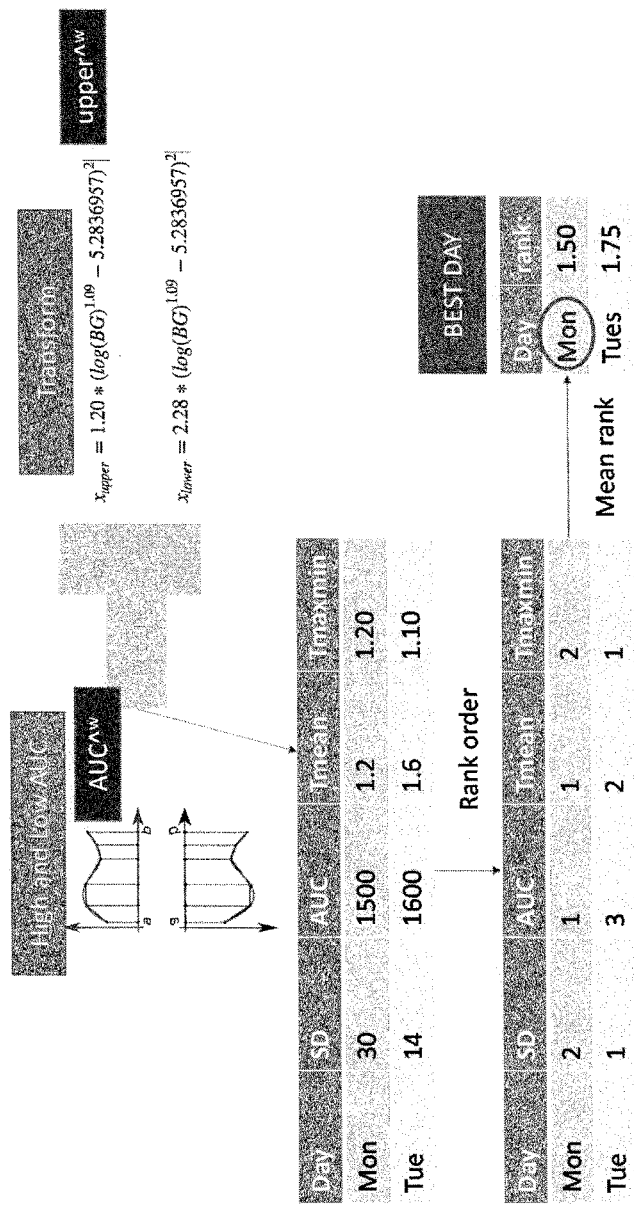
FIGS. 7 and 8 show charts reflecting how first and second weighting factors are applied, according to one embodiment.
Figure 8:
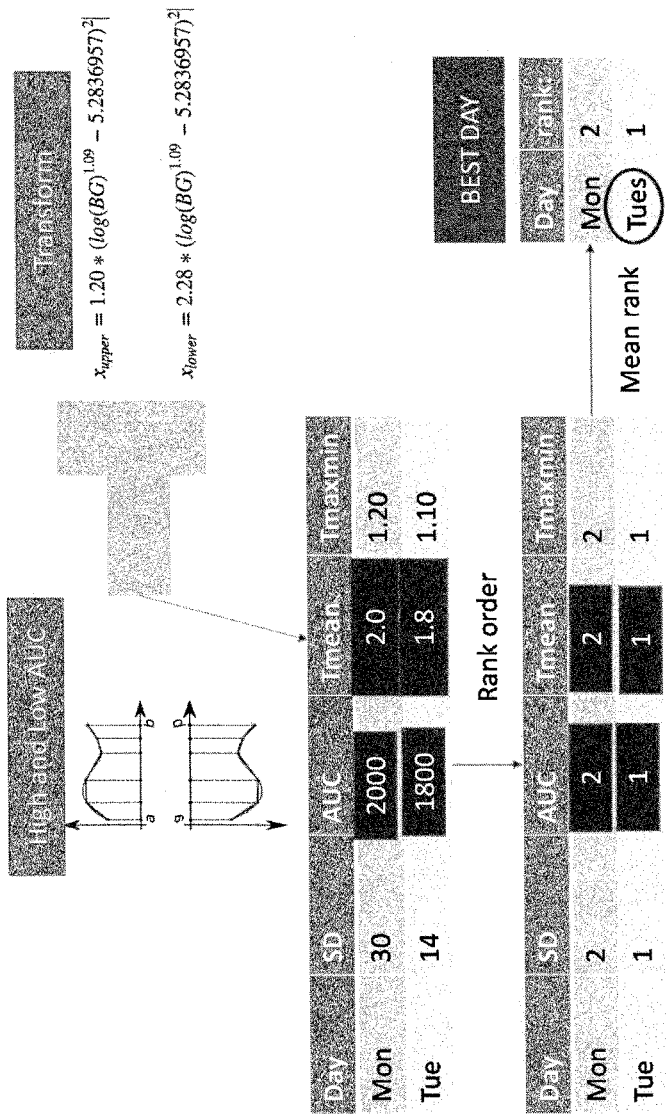

FIGS. 7 and 8 show charts reflecting how a weighting factor is applied, according to one embodiment.

In the example of FIGS. 7 and 8, feedback data was received from a secondary source, e.g. a source other than the user, the feedback data indicating that the previously determined highest ranked time period isn't the preferred highest ranked time period, together with a reason indicating that an average glucose level of the previously determined highest ranked time period is too high.

In one embodiment, the first weighting factor is applied to a high portion of the area under the curve, e.g. those glucose levels of the glucose subsamples of the current consideration set that are above an upper threshold of the area under the curve data associated with each glucose subsample of the current consideration set. In one embodiment, the upper threshold is 180. Thus, the first weighting factor is applied to the portion of the area under the curve represented by glucose data values that are above 180. Further, in this example, the first weighting factor is applied to that portion of the area under the curve by raising a value of that portion of the area under the curve to the power of $w_{pm}$. In one embodiment, the first weighting factor is applied to the high portion of the biotransform values as well. In one embodiment, a different weighting factor is applied to the high portion of the biotransform values. In a different, but similar, example, if a reason provided with the feedback data includes an average glucose of the previously determined highest ranked time period being too low, a second weighting factor is applied, in one embodiment, to a low portion, e.g. those glucose levels of the glucose subsamples of the current consideration set that are below a lower threshold of the area under the curve data associated with each glucose subsample of the current consideration set. In one embodiment, to determine which glucose data values of a given glucose subsample are used to determine the second weighting factor, the glucose data values of the given glucose subsample are first sorted from high to low. In one embodiment, the second weighting factor is determined using the lowest and second-lowest glucose level values of the given glucose data sample, for $x_i$ and $x_{i+1}$ respectively. In one embodiment, the lower threshold is 70. Thus, the second weighting factor is applied to the portion of the area under the curve represented by the glucose data values that are below 70. Further, in this example, the second weighting factor is applied to that portion of the area under the curve by raising a value of that portion of the area under the curve to the power of $w_{pm}$, as one example. In one embodiment, the second weighting factor is applied to the low portion of the biotransform values as well. In one embodiment, a different weighting factor is applied to the low portion of the biotransform values. In one embodiment, if glucose data values have changed due to weighting factors being applied to them, or for any other reason, the factors that depend on those glucose data values are determined again as well, as described herein.

Referring to FIGS. 7 and 8 together, applying the same weighting factor to the appropriate area under the curve and biotransform values results in the new highlighted values, resulting in a new ranking of the glucose subsamples of the current consideration set. Using the new glucose subsample rankings and the associated new highest ranked time period, activity data associated with the new highest ranked time period is developed. In the example, Tuesday has been determined to be the new highest ranked time period. Thus, activity data associated with Tuesday is copied or otherwise used to produce one or more user interfaces reflecting that Tuesday was a "best day" and emphasizing activities performed on Tuesday, with the intent that the user perform one or more of the Tuesday activities more frequently.

Figure 9:
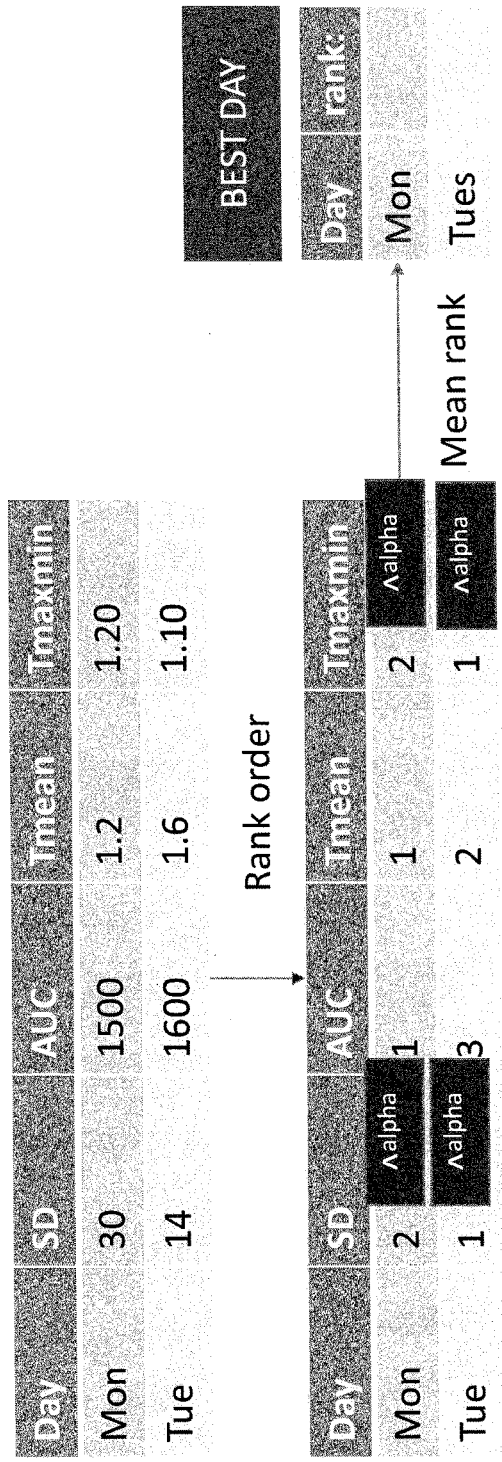

FIGS. 9 and 10 show charts reflecting how a third weighting factor is applied, according to one embodiment.

Referring to FIGS. 9 and 10 together, a third example of applying a weighting factor is presented.

In one embodiment, a third weighting factor is determined and applied to standard deviation and max-min data associated with each glucose subsample of the current consideration set.

Any desired weighting factor may be used. In one embodiment, the first weighting factor is of the form $$a_{pm} = 1 + \left| \frac{r_b - r_{b+1}}{n_{days}} \right|$$

where $r_b$ and $r_{b+1}$ respectively refer to rankings of the glucose subsamples. In one embodiment, the third weighting factor is applied at block 320 to the standard deviation factor previously determined at block 310. If desired, more than one weighting factor is determined, and each are applied to different factors or portions of glucose data included in various glucose subsamples.

In the example of FIGS. 9 and 10, feedback data was received from a secondary source, e.g. a source other than the user, the feedback data indicating that the determined highest ranked time period isn't the preferred highest ranked time period, together with a reason indicating that the variability or variance of glucose levels of the previously determined highest ranked time period is too high.

In one embodiment, the third weighting factor is applied to the previously determined standard deviations of the glucose subsamples of the current consideration set. Further, in this example, the third weighting factor is applied to the standard deviations by raising a value of the standard deviations to the power of $a_{pm}$, as one example. In one embodiment, the third weighting factor is applied to the min-max values as well. In one embodiment, a different weighting factor is applied to the min-max values.

Referring to FIGS. 9 and 10 together, applying a weighting factor to the standard deviation values and the min-max values results in the new highlighted values, resulting in a new ranking of the glucose subsamples. Using the new glucose subsample rankings and the associated new highest ranked time period, activity data associated with the new highest ranked time period is developed. In the example, Tuesday has been determined to be the new highest ranked time period. Thus, activity data associated with Tuesday is copied or otherwise used to produce one or more user interfaces reflecting that Tuesday was the "best day" and emphasizing activities performed on Tuesday, with the intent that the user perform one or more of the Tuesday activities more frequently.

In one embodiment, weighting factors are stored and applied to future glucose data and/or factors associated with subsamples associated with that glucose data. In this way, learning that takes place with respect to one group of glucose subsamples may be used to fine tune the process, thus providing more accurate results in later iterations.

At block 322, the process exits awaiting new data.

In one embodiment, a process for determining and providing activity recommendations is a computing application or process and may be stored, in full, or in part on a computer program product. Herein, a computer program product comprises a medium and/or I/O device configured to store or transport computing system readable code, whether available or known at the time of filing or as later developed.

Some examples of computer program products are CD's, DVD's, ROM cards, floppy discs, magnetic tapes, computer hard drives, portable hard drives, flash memory, volatile and non-volatile memory sticks, servers and databases on a network, or other media or process capable of delivering computer readable data representing computer readable code, whether available or known at the time of filing or as later developed. This medium may belong to a computing system. However, in some embodiments, the medium also may be removable and/or remote from the computing system.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "obtaining", "specifying", "identifying", "determining", "calculating", "using", "aggregating", "analyzing", "defining", "storing", "saving", "displaying", "categorizing", "providing", "processing", "accessing", "generating" etc., refer to the action and processes of a computing system or similar electronic device that manipulates and operates on data represented as physical (electronic) quantities within the computing system memories, resistors, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the drawing figures for method and apparatus and/or process or application for processing information discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented method for determining and providing activity recommendations comprising:

receiving, from at least one glucose collection device associated with an individual, glucose level data representing a plurality of glucose level readings taken from the individual over a time span;

forming, from the glucose level data representing the plurality of glucose level readings, a plurality of subsamples of glucose level data, each subsample of glucose level data comprising glucose level data representing individual glucose levels of the plurality of glucose levels taken within a given time period associated with the subsample, receiving, from an activity data source associated with the individual, activity data representing one or more activities performed by the individual, with at least one activity being received for each of the time periods associated with the subsamples;

determining, for each subsample, an average area under the curve associated with the glucose levels of the subsample;

determining, for each subsample, a standard deviation of the glucose readings of the subsample;

performing, for each subsample, a biotransform algorithm on each individual glucose reading of the subsample;

determining, for each subsample, a min-max total associated with the glucose readings of the subsample;

ranking each subsample against each other subsample, the rankings being at least partly based on the average area under the curve for each subsample, the standard deviation for each subsample, the biotransform for each subsample and the min-max total for each subsample;

determining a highest ranked time period associated with a highest ranked subsample;

determining one or more activities of the activity data representing one or more activities performed by the individual that were performed within the determined highest ranked time period; and recommending that the individual increase a number of instances which the one or more determined activities are performed.

2. The computing system implemented method of claim 1 further wherein each subsample covers a different 24-hour period.

3. The computing system implemented method of claim 1 further wherein each subsample covers a 24-hour period corresponding to a day of a week.

4. The computing system implemented method of claim 1 further comprising defining a glucose range having an upper threshold glucose level and a lower threshold glucose level, the upper threshold glucose level being a higher amount of glucose above which is considered to be undesirable, the lower threshold glucose level being a lower amount of glucose below which is considered to be undesirable;

further wherein the biotransform algorithm takes into consideration the upper and lower threshold glucose levels.

5. The computing system implemented method of claim 1 wherein the biotransform algorithm places increased emphasis on glucose levels below the lower threshold glucose level as compared with an emphasis placed on glucose levels above the upper threshold glucose level.

6. The computing system implemented method of claim 1 further wherein the upper threshold glucose level is between 110 and 130.

7. The computing system implemented method of claim 4 further wherein the upper threshold glucose level is 120.

8. The computing system implemented method of claim 1 further wherein the lower threshold glucose level is between 60 and 80.

9. The computing system implemented method of claim 1 further wherein the lower threshold glucose level is 70.

10. The computing system implemented method of claim 1 wherein the glucose collection device is a continuously monitoring glucose collection device which samples glucose levels of the individual at least 100 times per time period.

11. The computing system implemented method of claim 10 wherein the glucose collection device is a continuously monitoring glucose collection device which samples glucose of the individual between 100 and 300 times per time period.

12. The computing system implemented method of claim 10 wherein the average area under the curve associated with the glucose levels of the subsample is determined by,
for each two consecutive glucose level values:
for individual ones of the two consecutive glucose level values that is above 180, subtract 180 and use the transformed result in further area under the curve operations;
for individual ones of the two consecutive glucose level values that are below the lower threshold glucose level, subtract the lower threshold glucose level, square the result, and use the squared result in further area under the curve operations; and
combine a value of the first of the two consecutive glucose levels with a value of the second of the two consecutive glucose levels, multiply with a length of time that occurred between the two readings being taken, and divide the result by two; and
add all of the individual areas under the curve together and divide by the number of individual areas under the curve being added together, resulting in an average area under the curve.

13. The computing system implemented method of claim 1 wherein ranking each subsample against each other for each glucose reading data set includes individually numerically ranking each subsample against each other subsample on the average area under the curve;
individually numerically ranking each subsample against each other subsample on the standard deviation of the subsample;
individually numerically ranking each subsample against each other subsample on the results of performing a biotransform algorithm;
individually numerically ranking each subsample against each other subsample on the min-max total;
for each given subsample, combining the numerical rankings of the subsample with respect to average area under the curve, standard deviation, the results of performing a biotransform algorithm and the min-max total, resulting in a combined ranking for the given subsample; and
for each given subsample, dividing the combined ranking for the given glucose reading data set by four resulting in an overall subsample ranking for the given subsample.

14. A nontransitory computer-readable medium having stored thereon computer-executable instructions which, when executed by a computing processor, perform a process for determining and providing activity recommendations, the process comprising:
receiving, from at least one glucose collection device associated with an individual, glucose level data representing a plurality of glucose level readings taken from the individual over a plurality of time periods;
forming, from the glucose level data representing the plurality of glucose level readings, a plurality of subsamples of glucose levels data, each subsample of glucose level data comprising glucose levels data representing individual glucose levels of the plurality of glucose levels taken within a given time period,
receiving, from an activity data source associated with the individual, activity data representing one or more activities performed by the individual, with at least one activity being received with respect to each of the time periods;
determining, for each subsample, an average area under the curve associated with the glucose levels of the subsample;
determining, for each subsample, a standard deviation of the glucose readings of the subsample;
performing, for each subsample, a biotransform algorithm on each individual glucose reading of the subsample;
determining, for each subsample, a min-max total associated with the glucose readings of the subsample;
ranking each subsample against each other subsample, the rankings being at least partly based on the average area under the curve for each subsample, the standard deviation for each subsample, the biotransform for each subsample and the min-max total for each subsample;
determining a highest ranked time period associated with a highest ranked subsample;
determining one or more activities of the activity data representing one or more activities performed by the individual that were performed within the determined highest ranked time period; and
recommending that the individual increase a number of instances which the one or more determined activities are performed.

15. The computing system implemented method of claim 14 further wherein each time period covers a 24-hour period.

16. The computing system implemented method of claim 14 further wherein each time period covers a 24-hour period corresponding to a day of a week.

17. The computing system implemented method of claim 14 further comprising defining a glucose range having an upper threshold glucose level and a lower threshold glucose level, the upper threshold glucose level being a higher amount of glucose above which is considered to be undesirable, the lower threshold glucose level being a lower amount of glucose below which is considered to be undesirable;
further wherein the biotransform algorithm takes into consideration the upper and lower threshold glucose levels.

18. The computing system implemented method of claim 17 wherein the biotransform algorithm places increased emphasis on glucose levels below the lower threshold glucose level as compared with an emphasis placed on glucose levels above the upper threshold glucose level.

19. The computing system implemented method of claim 17 further wherein the upper threshold glucose level is between 110 and 130.

20. The computing system implemented method of claim 17 further wherein the upper threshold glucose level is 120.

21. The computing system implemented method of claim 17 further wherein the lower threshold glucose level is between 60 and 80.

22. The computing system implemented method of claim 17 further wherein the lower threshold glucose level is 70.

23. The computing system implemented method of claim 14 wherein the glucose collection device is a continuously monitoring glucose collection device which samples glucose levels of the individual at least 100 times per time period.

24. The computing system implemented method of claim 23 wherein the glucose collection device is a continuously monitoring glucose collection device which samples glucose of the individual between 100 and 300 times per time period.

25. The computing system implemented method of claim 14 wherein the average area under the curve associated with the glucose levels of the subsample is determined by,
for each two consecutive glucose level values:
for individual ones of the two consecutive glucose level values that is above 180, subtract 180 and use the transformed result in further area under the curve operations;
for individual ones of the two consecutive glucose level values that are below the lower threshold glucose level, subtract the lower threshold glucose level, square the result, and use the squared result in further area under the curve operations; and
combine a value of the first of the two consecutive glucose levels with a value of the second of the two consecutive glucose levels, multiply with a length of time that occurred between the two readings being taken, and divide the result by two; and
add all of the individual areas under the curve together and divide by the number of individual areas under the curve being added together, resulting in an average area under the curve.

26. The computing system implemented method of claim 14 wherein ranking each glucose reading data set against each other for each glucose reading data set includes
individually numerically ranking each subsample against each other subsample on the average area under the curve;
individually numerically ranking each subsample against each other subsample on the standard deviation of the subsample;
individually numerically ranking each subsample against each other subsample on the results of performing a biotransform algorithm;
individually numerically ranking each subsample against each other subsample on the min-max total;
for each given subsample, combining the numerical rankings of the subsample with respect to average area under the curve, standard deviation, the results of performing a biotransform algorithm and the min-max total, resulting in a combined ranking for the given subsample; and
for each given subsample, dividing the combined ranking for the given glucose reading data set by four resulting in an overall subsample ranking for the given subsample.

27. A system for determining and providing activity recommendations, comprising:
one or more computing processors;
one or more memories operatively coupled the one or more computing processors, the one or more memories having stored therein computing processor executable instructions which when executed by the one or more computing processors perform a process for determining and providing activity recommendations comprising:
receiving, from at least one glucose collection device associated with an individual, glucose level data representing a plurality of glucose level readings taken from the individual over a plurality of time periods;
forming, from the glucose level data representing the plurality of glucose level readings, a plurality of subsamples of glucose levels data, each subsample of glucose level data comprising glucose levels data representing individual glucose levels of the plurality of glucose levels taken within a given time period,
receiving, from an activity data source associated with the individual, activity data representing one or more activities performed by the individual, with at least one activity being received with respect to each of the time periods;
determining, for each subsample, an average area under the curve associated with the glucose levels of the subsample;
determining, for each subsample, a standard deviation of the glucose readings of the subsample;
performing, for each subsample, a biotransform algorithm on each individual glucose reading of the subsample;
determining, for each subsample, a min-max total associated with the glucose readings of the subsample;
ranking each subsample against each other subsample, the rankings being at least partly based on the average area under the curve for each subsample, the standard deviation for each subsample, the biotransform for each subsample and the min-max total for each subsample;
determining a highest ranked time period associated with a highest ranked subsample;
determining one or more activities of the activity data representing one or more activities performed by the individual that were performed within the determined highest ranked time period; and
recommending that the individual increase a number of instances which the one or more determined activities are performed.

28. The computing system implemented method of claim 27 further wherein each time period covers a 24-hour period.

29. The computing system implemented method of claim 27 further wherein each time period covers a 24-hour period corresponding to a day of a week.

30. The computing system implemented method of claim 27 further comprising defining a glucose range having an upper threshold glucose level and a lower threshold glucose level, the upper threshold glucose level being a higher amount of glucose above which is considered to be undesirable, the lower threshold glucose level being a lower amount of glucose below which is considered to be undesirable;
further wherein the biotransform algorithm takes into consideration the upper and lower threshold glucose levels.

31. The computing system implemented method of claim 30 wherein the biotransform algorithm places increased emphasis on glucose levels below the lower threshold glucose level as compared with an emphasis placed on glucose levels above the upper threshold glucose level.

32. The computing system implemented method of claim 30 further wherein the upper threshold glucose level is between 110 and 130.

33. The computing system implemented method of claim 30 further wherein the upper threshold glucose level is 120.

34. The computing system implemented method of claim 30 further wherein the lower threshold glucose level is between 60 and 80.

35. The computing system implemented method of claim 30 further wherein the lower threshold glucose level is 70.

36. The computing system implemented method of claim 27 wherein the glucose collection device is a continuously monitoring glucose collection device which samples glucose levels of the individual at least 100 times per time period.

37. The computing system implemented method of claim 36 wherein the glucose collection device is a continuously monitoring glucose collection device which samples glucose of the individual between 100 and 300 times per time period.

38. The computing system implemented method of claim 27 wherein the average area under the curve associated with the glucose readings of the set is determined by, for each two consecutive glucose level values:
> for individual ones of the two consecutive glucose level values that is above 180, subtract 180 and use the transformed result in further area under the curve operations;
> 
> for individual ones of the two consecutive glucose level values that are below the lower threshold glucose level, subtract the lower threshold glucose level, square the result, and use the squared result in further area under the curve operations; and
> 
> combine a value of the first of the two consecutive glucose levels with a value of the second of the two consecutive glucose levels, multiply with a length of time that occurred between the two readings being taken, and divide the result by two; and add all of the individual areas under the curve together and divide by the number of individual areas under the curve being added together, resulting in an average area under the curve.

39. The computing system implemented method of claim 27 wherein ranking each subsample against each other glucose reading data set includes individually numerically ranking each subsample against each other subsample on the average area under the curve;

> individually numerically ranking each subsample against each other subsample on the standard deviation of the subsample;
> 
> individually numerically ranking each subsample against each other subsample on the results of performing a biotransform algorithm;
> 
> individually numerically ranking each subsample against each other subsample on the min-max total;
> 
> for each given subsample, combining the numerical rankings of the subsample with respect to average area under the curve, standard deviation, the results of performing a biotransform algorithm and the min-max total, resulting in a combined ranking for the given subsample; and
> 
> for each given subsample, dividing the combined ranking for the given glucose reading data set by four resulting in an overall subsample ranking for the given subsample.

* * * * *